(12) United States Patent
Zaldivar et al.

(10) Patent No.: US 8,858,070 B2
(45) Date of Patent: Oct. 14, 2014

(54) SYSTEM AND METHOD FOR MEASURING GLASS TRANSITION TEMPERATURE

(75) Inventors: Rafael J. Zaldivar, Huntington Beach, CA (US); James P. Nokes, Torrance, CA (US)

(73) Assignee: The Aerospace Corporation, El Segundo, CA (US)

( * ) Notice: Subject to any disclaimer, the term of this patent is extended or adjusted under 35 U.S.C. 154(b) by 411 days.

(21) Appl. No.: 13/153,168

(22) Filed: Jun. 3, 2011

(65) Prior Publication Data

US 2012/0307860 A1 Dec. 6, 2012

(51) Int. Cl.
G01N 25/12 (2006.01)
G01N 25/04 (2006.01)
G01N 13/02 (2006.01)

(52) U.S. Cl.
CPC ........ *G01N 25/04* (2013.01); *G01N 2013/0208* (2013.01)
USPC .................................... 374/16; 374/6; 374/45

(58) Field of Classification Search
USPC ............................................ 422/51; 438/147
See application file for complete search history.

(56) References Cited

U.S. PATENT DOCUMENTS

| | | | |
|---|---|---|---|
| 3,661,579 A * | 5/1972 | Vrancken et al. | 430/294 |
| 4,909,971 A * | 3/1990 | Coughlin et al. | 264/45.5 |
| 4,916,043 A * | 4/1990 | Nagumo et al. | 430/203 |
| 5,354,613 A * | 10/1994 | Quintens et al. | 428/341 |
| 5,962,571 A * | 10/1999 | Overbeek et al. | 524/460 |
| 7,048,434 B2 * | 5/2006 | Tregub et al. | 374/10 |
| 7,643,717 B2 * | 1/2010 | Rantala et al. | 385/126 |
| 8,114,951 B2 * | 2/2012 | James et al. | 528/182 |
| 2004/0202700 A1 * | 10/2004 | Phaneuf et al. | 424/443 |
| 2005/0208441 A1 * | 9/2005 | Oyamada et al. | 430/619 |
| 2006/0046216 A1 * | 3/2006 | Suzuki | 430/619 |
| 2009/0220753 A1 * | 9/2009 | Sugasaki | 428/195.1 |
| 2011/0182946 A1 * | 7/2011 | Johnston et al. | 424/400 |
| 2011/0261443 A1 * | 10/2011 | Isojima et al. | 359/360 |
| 2012/0082836 A1 * | 4/2012 | Sugasaki | 428/220 |
| 2013/0028955 A1 * | 1/2013 | Tolia | 424/450 |
| 2013/0251948 A1 * | 9/2013 | Lyons et al. | 428/148 |
| 2013/0266762 A1 * | 10/2013 | Mayers et al. | 428/141 |

FOREIGN PATENT DOCUMENTS

WO    WO 2010022124 A1 *   8/2008

OTHER PUBLICATIONS

Zaldivar, Rafael J. et al., "Effect of Processing Parameter Changes on the Adhesion of Plasma-treated Carbon Fiber Reinforced Epoxy composites", Journal of Composite Materials, Dec. 2010, pp. 1435-1454 vol. 44, Sage Publishing Company, UK www.sagepub.co.uk.

* cited by examiner

*Primary Examiner* — Gail Kaplan Verbitsky
(74) *Attorney, Agent, or Firm* — Paul D. Chancellor; Ocean Law

(57) ABSTRACT

A system and method for measuring a glass transition temperature of a hydrophobic polymer having a surface tagged with an atmospheric plasma.

10 Claims, 7 Drawing Sheets

| Temperature (Degrees C) | Contact Angle (Degrees) |
|---|---|
| 25 | 16 |
| 60 | 15 |
| 80 | 19 |
| 100 | 20 |
| 120 | 23 |
| 140 | 65 |
| 150 | 87 |
| 175 | 95 |
| 200 | 95 |

SYSTEM AND METHOD FOR MEASURING GLASS TRANSITION TEMPERATURE

BACKGROUND OF THE INVENTION

1. Field of the Invention

The invention relates to measurement of physical properties of matter. In particular, the invention relates to a system and method for measuring a glass transition temperature of a material such as a polymer or a composite incorporating a polymer.

2. Discussion of the Related Art

Advanced structures frequently incorporate polymers such as epoxy resins and exhibit a "glass transition temperature" commonly designated as "Tg". The glass transition temperature of a material is useful for indicating its state, the degree of cure, effectiveness of curing agents, and softening point at elevated temperatures.

As a polymer is heated, it undergoes a transition similar to a thermodynamic second order transition. This involves a discontinuous change in a secondary thermodynamic quantity such as the expansion coefficient or heat capacity. The Tg is often referred to as the temperature region wherein a polymer goes from a glassy state to a rubbery state. Typically, the material will undergo a modulus change that can range over three orders of magnitude through this region. In resin systems, the Tg is influenced by, among other things, the composition of the resin molecule, the cross-link density, the polar nature of the resin molecule's functional groups, the curing agent or catalyst, and the cure time and temperature.

A material's glass transition temperature Tg therefore provides information about degree of cure of a resin and whether the formulation was properly prepared. As such, Tg is one of the most important quality control properties of a neat resin and/or composite. There are numerous examples in the development and failure analysis of composite hardware where problems attributable to chemistry, contamination, and processing were identified by the use of this test.

Known Tg measurement methods include those based on the material's heat capacity, its coefficient of thermal expansion, and its modulus of elasticity. These methods and some of their limitations are discussed below.

The Tg of a specimen can be tested using differential scanning calorimetry ("DSC"). In this process, changes in heat capacity can help identify the Tg as a function of temperature. However, in filled systems or composites, the reduced volume of the material that is typically analyzed will produce only a limited DSC signal that is often not very discrete.

The Tg can also be measured by following the coefficient of thermal expansion ("CTE") for a resin using thermal mechanical analysis ("TMA"). A discontinuous change in CTE as a function of temperature usually indicates Tg. TMA characterizations are suitable for thicker unreinforced specimens. Notably, measuring CTE variations in high fiber volume composite materials with low CTE values is a much more complex and difficult task to perform.

Dynamic mechanical analysis ("DMA") is one of the most commonly used techniques for Tg determination. DMA measures the response of a material to a sinusoidal or other periodic stress. Since the stress and strain are usually not in phase, two quantities can be determined: a modulus and a phase angle. Since the material usually undergoes a large drop in modulus through the Tg, the instrument can identify this point. This test is typically limited to specimens of a specific thickness and dimension (i.e. 1.0"×1.5"×0.25"). However, thin films are typically quite difficult to measure as are differences between localized areas.

SUMMARY OF THE INVENTION

The present inventors ("Inventors") have shown by experiment that tagging the surface of a polymer and following surface changes provides an indication of glass transition temperature "Tg." Some embodiments of the invention appear below.

Methods for determining the glass transition temperature Tg of hydrophobic polymers including composites and thin resin films have been invented. The Tg is one of the most important inherent properties of a polymer. It is an excellent quality control (QC) metric that can be used to evaluate the mechanical and thermal behavior of a polymer. Measuring the Tg of thin (<10 µm) resin films as well as localized areas on composite surfaces is typically a difficult, if not an impossible task to perform. In the technique now presented, the surface of the resin material is tagged by the use of atmospheric plasma. The Inventors' data shows that plasma treatment incorporates specific oxygen containing groups on the outer surface of the treated substrate. This treatment promotes the wetting characteristics of otherwise very hydrophobic systems by increasing the surface free energy. The surface free energy can be accurately evaluated using contact angle measurements.

The Inventors' work includes discovering that if one measures the initial contact angle of the treated surface and progressively heats the sample, the contact angle remains essentially the same until the resin temperature approaches its Tg. At this point, changes in surface chemistry translate into an uncharacteristically large increase in contact angle. The transition from wetting to non-wetting creates an inflection point that can be used to determine the Tg of the system and is very similar to the thermal profile observed using dynamic mechanical analysis (DMA). The largest transition in wetting angle with temperature coincides with the Tg of the material. The Inventors' work suggests that at the Tg, the substrate becomes compliant enough so that the surface groups that were initially anchored to the substrate now achieve sufficient mobility to reorient themselves to minimize surface energy. This reorientation can be monitored by measuring the contact angle of the surface. Several composites have been tested with varying Tg's and correlate well with Tg's reported by conventional methods such as differential scanning calorimetry (DSC) and dynamic mechanical analysis (DMA). These tested composites include polycyanurate (RS3C)/M55J Pan-based carbon fiber composite, a 177 degree C. cured system, and TC410, a 121 degree C. cured system. The size of the contact angle droplets can be controlled so as to quantify the Tg's of localized areas. The method is also useful for determining the Tg on the surface of resins and composites, a task typically difficult to perform by other methods. In addition, a variation in filler concentration and/or type of reinforcement (e.g. fibers, particulates, etc.) does not appear to affect the characterization using this method. The changes in contact angle appear to be primarily influenced by only the matrix material.

The invention is applicable to polymeric material surfaces including the surfaces of polymeric films, cast resins, and/or composites. Typically, the vast majority of resins are hydrophobic and do not wet. Therefore, their initial contact angles are high and do not improve with temperature or after thermal exposure. The Inventors' data describes the types of surface groups incorporated on the surface of the polymer after treatment. This treatment creates a polar surface which is compatible with water and thus promotes surface wetting yielding a low contact angle. The specimen is then heated and the surface is characterized using contact angle measurements. In various embodiments, tagging the surface of the material to follow changes in surface characteristics to determine Tg provides a unique feature of the invention. Non-plasma treated polymeric composites would otherwise not show changes in contact angle as a function of temperature. Other measurements as a function of treatment, such as DMA and DSC, could also be performed to observe what we perform using contact angle measurements. However, contact angle measurements are quick and inexpensive to perform and correlate with the chemical changes observed on the very outer surfaces of the material investigated. The region where the material shows a large increase in contact angle as a function of temperature coincides with the Tg of that material.

BRIEF DESCRIPTION OF THE DRAWINGS

The present invention is described with reference to the accompanying figures. These figures, incorporated herein and forming part of the specification, illustrate the present invention and, together with the description, further serve to explain the principles of the invention and to enable a person skilled in the relevant art to make and use the invention.

FIG. 6 shows temperature and contact angle data the Inventors collected from a plurality of samples for use in the method of FIG. 1.

DETAILED DESCRIPTION OF THE PREFERRED EMBODIMENTS

Figure 1:
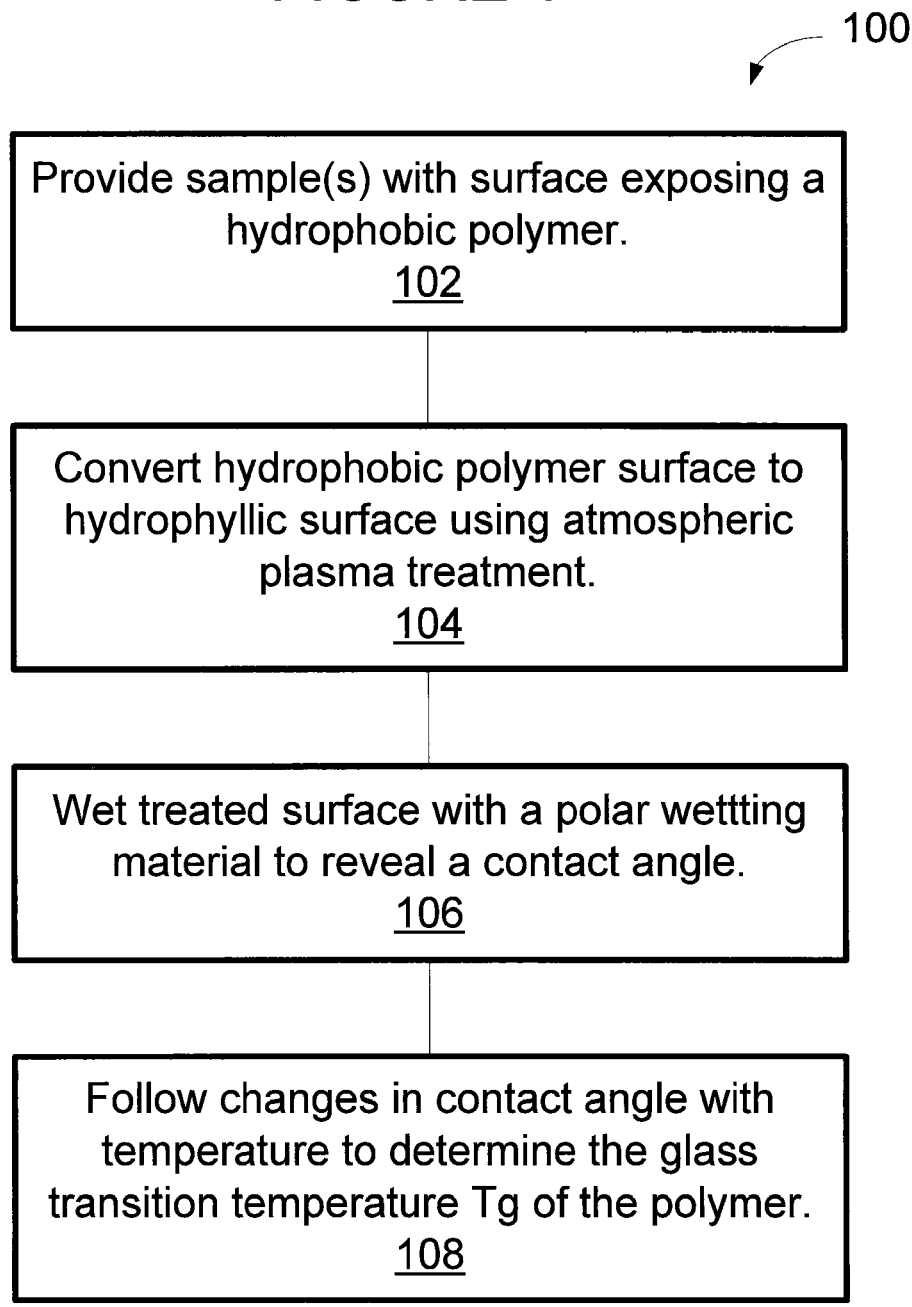
FIG. 1 shows a glass transition temperature determination method in accordance with the present invention.

FIG. 1 shows a glass transition temperature determination method in accordance with the present invention 100. A sample having a surface exposing a hydrophobic polymer is provided 102. The sample's hydrophobic surface is converted to a hydrophilic surface via an atmospheric plasma treatment 104. The treated surface is wetted using a polar wetting material to reveal a contact angle 106. Contact angle variations with sample temperature are then used to determine the glass transition temperature of the polymer 108. As will be described in further detail below, embodiments of this method utilize a single sample and embodiments of this method utilize a plurality of samples. Persons of ordinary skill in the art will recognize the selection of wetting materials, such as water and glycol, is in accordance with expected glass transition temperatures. For example, where a Tg greater than 100 degrees C. is anticipated, a wetting material such as glycol would be selected.

In various embodiments, the mentioned sample 102 is any of a complete part, structure, or device, or a portion of a part, structure, or device. For example, the sample might be a portion of a structural member such as a beam, column, or frame. In some embodiments, the sample is a surface sample removed from the surface of a larger member; for example, a scooped out portion. And, in some embodiments, the sample is a full sample extending across a surface of a larger member; for example, a mid-section of a beam. In various embodiments, a surface of a material is exposed and a Tg related to the exposed surface is evaluated.

Figure 2:
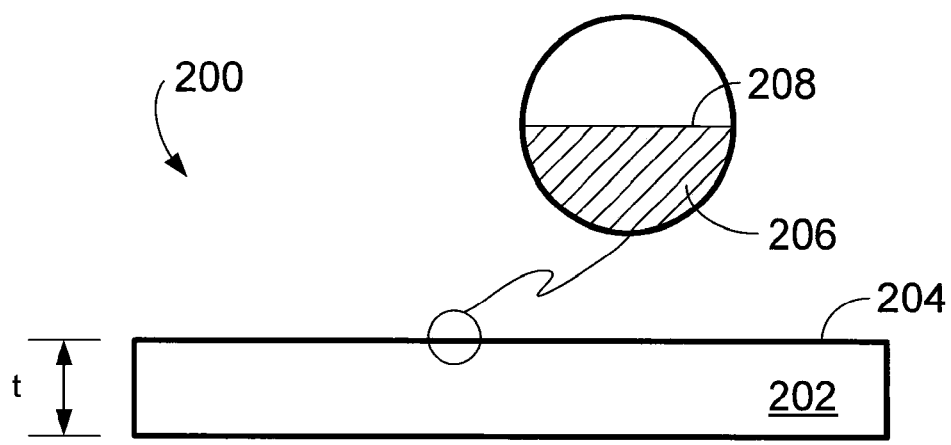
FIG. 2 illustrates a sample for use in the method of FIG. 1.

FIG. 2 shows a sample to be tested 200. The sample 202 includes a bare surface 204 and at least a portion of the bare surface 208 exposes a hydrophobic polymeric material 206. Suitable polymeric materials are low energy solids characterized by molecules having attractive forces that are weak in comparison to chemical bonds. Exemplary polymers include hydrophobic resins containing a non-polar functional group, such as an alkane or aromatic group.

In various embodiments, the sample 202 is a thin (t<10 µm) polymeric or resin film, cast resin, and/or a composite such as a localized area on a composite structure. Exemplary resins include epoxides and polycyanurates such as cyanate esters. In various embodiments, localized area refers to an area approximately the size of the wetted area (see FIG. 4 below). In various embodiments, localized area refers to the area wetted by the wetting material 402.

Figure 3:
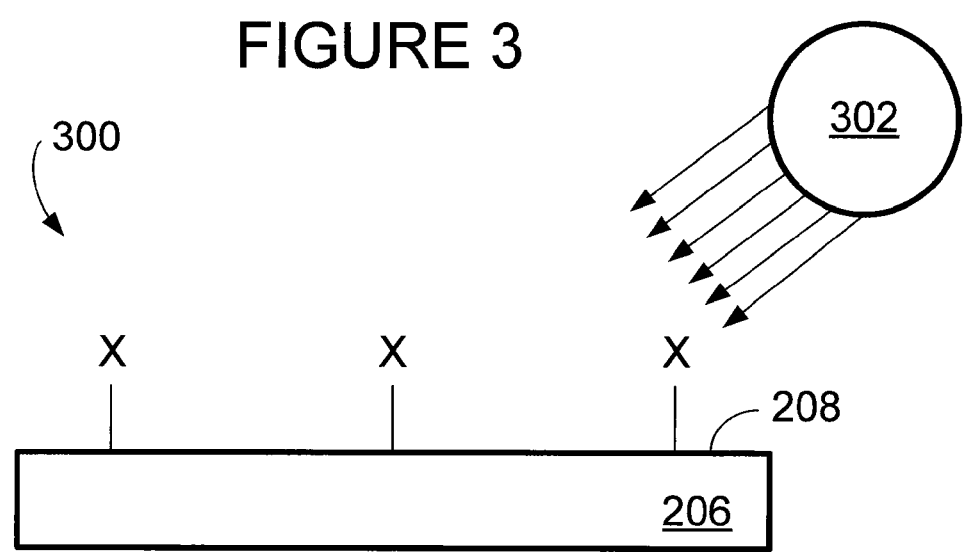
FIG. 3 illustrates a hydrophobic polymeric material of a sample to be tested for use in the method of FIG. 1.

FIG. 3 shows a treated sample 300. Here, the sample test surface 204, including the bare surface portion 208, has been treated with an atmospheric plasma 302. The plasma treatment incorporates specific oxygen containing groups "X" on a surface, here on the sample test surface 204 and in particular on the bare surface portion 208 (as shown by attached X groups); in other words, the plasma treatment "tags" the polymer.

In an embodiment, the group X denotes an oxygen atom bound with a hydrogen atom. Test data indicate the degree of atmospheric plasma treatment is not critical because oxygen groups are typically incorporated after minimal exposure; exemplary exposures include one to three treatment passes using a plasma torch operating at a plasma power level of 96 watts, gas flows of 15 liters/minute He and 0.4 liters/minute $O_2$, and a working distance of 1 millimeter. Persons of ordinary skill in the art will recognize other atmospheric plasma treatments with differing conditions and constituent flowrates, and in cases additional constituents, are capable of incorporating the mentioned OH groups. For example, the publication by Zaldivar, R. J. et al (2010), *Effect of Processing Parameter Changes on the Adhesion of Plasma-treated Carbon Fiber Reinforced Epoxy composites, Journal of Composite Materials, Vol.* 44, 1435-1454 indicates additional suitable plasma treatments. Applicant now incorporates this publication in its entirety and for all purposes including its teaching of atmospheric plasma treatments.

Figure 4:
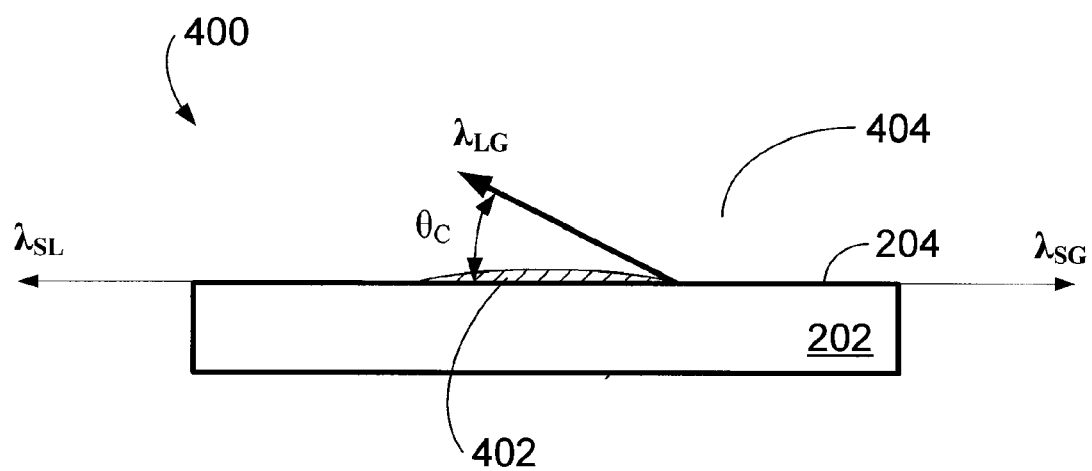
FIG. 4 illustrates a wetted sample for use in the method of FIG. 1.

FIG. 4 shows a wetted sample 400. Here, the treated test surface 204 is wetted with a wetting material 402. As shown, a contact angle $\theta_C$ is formed by the wetting material liquid at a three phase boundary where the wetting material 402, gas 404, and solid 202 intersect.

Interfacial tensions "λ" define the contact angle. In particular, the angle between $\lambda_{LG}$, interfacial tension at the liquid-gas interface, and $\lambda_{SG}$, interfacial tension at the solid-gas interface, is the contact angle $\theta_C$. The third interfacial tension shown is $\lambda_{SL}$, the interfacial tension at the solid-liquid interface. Young's Relation expresses the contact angle analytically where $\lambda_{SG} = \lambda_{SL} + \lambda_{LG} (\cos \theta)$.

Common methods for measuring contact angles of non-porous solids include optical tensiometry (goniometry) and force tensiometry. In optical tensiometry, a sessile drop of test liquid on a solid substrate is observed. Force tensiometry involves measuring the forces of interaction as a solid is contacted with a test liquid.

In optical tensiometry analysis of the shape of a drop of test liquid placed on a solid is the basis for determining the contact angle (optical tensiometry or goniometry). The basic elements of an optical tensiometer (also called contact angle meter) include a light source, sample stage, lens, and image capture. Contact angle can be assessed directly measuring the angle formed between the solid and the tangent to the drop surface. An exemplary goniometer is a rame'-hart (Netcong, N.J.) Advanced Automated Digital Goniometer.

Force tensiometer methods for measuring contact angles include the Du Noüy ring method, the Wilhelmy Plate method, and variants of these methods. Force tensiometer methods for measuring contact angles measure the forces that are present when a sample of solid is brought into contact with a test liquid. If the forces of interaction, geometry of the solid and surface tension of the liquid are known, the contact angle may be calculated. (See for example Biolin Scientific, Attenson Theta optical tensiometer Sigma series including Sigma 700/701.)

In an embodiment, the glass transition temperature is determined from a plurality of similar samples.

Figure 5:
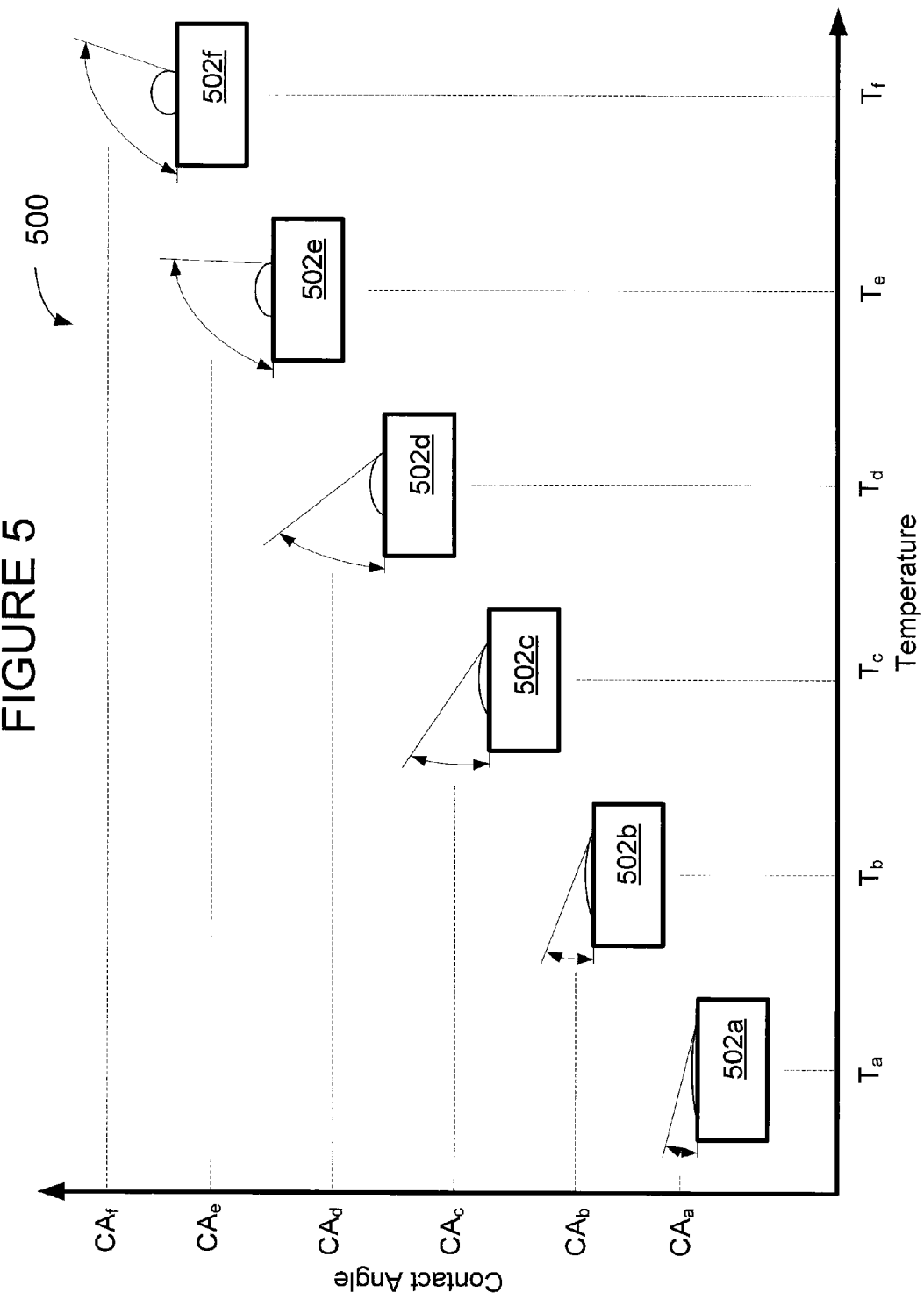
FIG. 5 shows a glass transition temperature test method with a plurality of samples for use in the method of FIG. 1.

FIG. 5 shows a glass transition temperature test method using a plurality of samples 500. Each of the samples 502a-f has, as described above, been treated with atmospheric plasma and wetted with a wetting material. In addition, each sample has been heated to a respective temperature $T_{a-f}$ producing a corresponding contact angle $CA_{a-f}$.

In various embodiments, knowledge and/or estimates of the glass transition temperature of the polymer involved indicate an appropriate temperature range $T_{a-f}$. For example, if the polymer's expected glass transition temperature is 120 degrees C., then setting the lower temperature $T_a$ to 60 degrees C. and the upper temperature $T_f$ to 180 degrees C. locates the glass transition temperature in the middle of this range.

Using the method illustrated in FIG. 5, the Inventors obtained the contact angle versus temperature data 600 presented in FIG. 6 for several identical samples of polycyanurate (RS3C)/M55J Pan-based carbon fiber composite. The data is plotted 700 in FIG. 7.

A curve drawn through the plotted data 700 includes a relatively sharply sloped central region in a range of approximately 110-150 degrees C. flanked by a less sharply sloped trailing region of the curve to the left of center in a range of approximately 25-110 degrees C., and a less sharply sloped leading region of the curve to the right of center in a range of approximately 150-200 degrees C.

The onset of the sharply sloped central region of the curve indicates the glass transition temperature Tg has been reached. In some embodiments, a curve inflection point indicates the Tg has been reached. In various embodiments, a transition at or near the junction of the sharply sloped central region of the curve and the less sharply sloped trailing end of the curve indicates a range of temperatures bounding the glass transition temperature.

Figure 7:
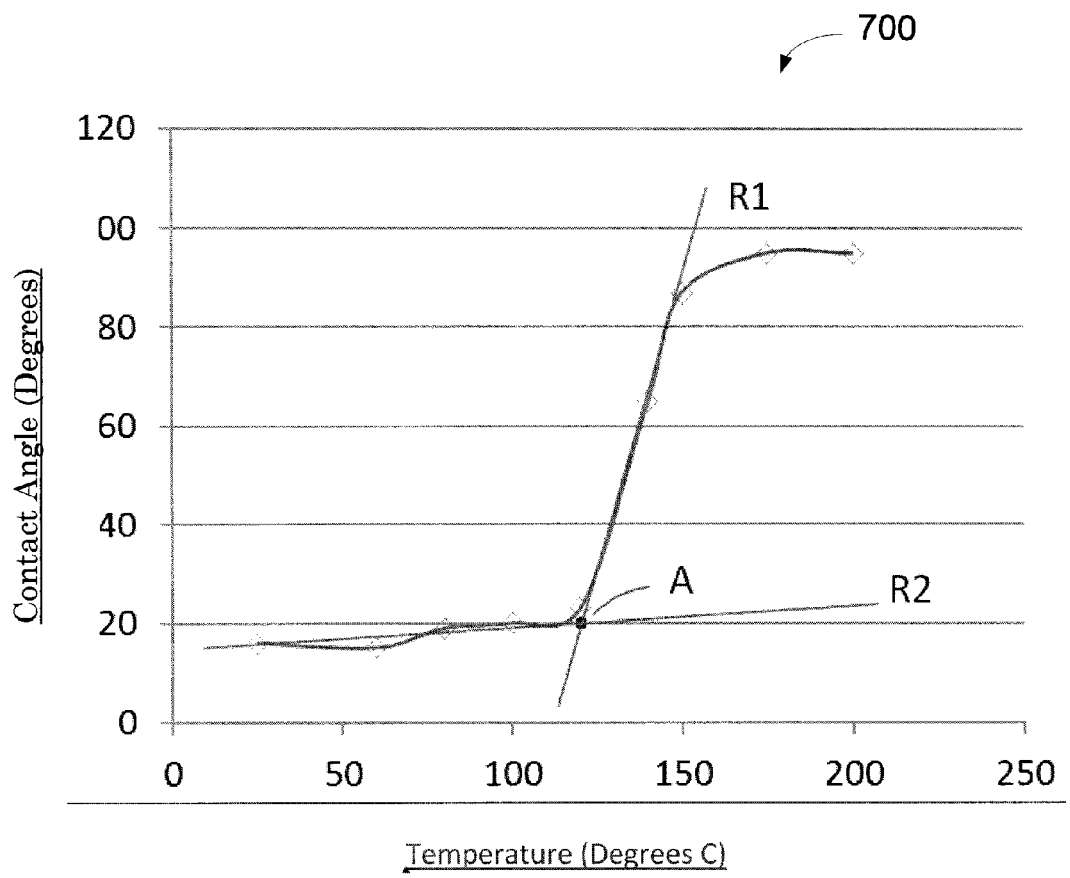
FIG. 7 shows a plot of the data of FIG. 6 for use in the method of FIG. 1.

In an embodiment, the glass transition temperature is indicated by intersection of two linear regression lines. As shown in FIG. 7, a first linear regression line for the central region of the curve R1 is drawn and intersects with a second linear regression line for the trailing region of the curve R2. Here, the intersection of the linear regression lines "A" indicates a glass transition temperature Tg of approximately 120 degrees C.

The data analysis described above, including plotting the data, observing the shape(s) of the curve, and use of linear regression provide but limited examples of available data analysis techniques that might be utilized to identify a transition and/or inflection point indicating a glass transition temperature. As persons of ordinary skill in the art will appreciate, these data analysis descriptions also suggest other available methods of data analysis that might be used including, for example, curve fitting techniques such as interpolating and approximating polynomials that provide a means of continuously evaluating curve slope and finding curve maxima, minima, and inflection points.

Figure 8:
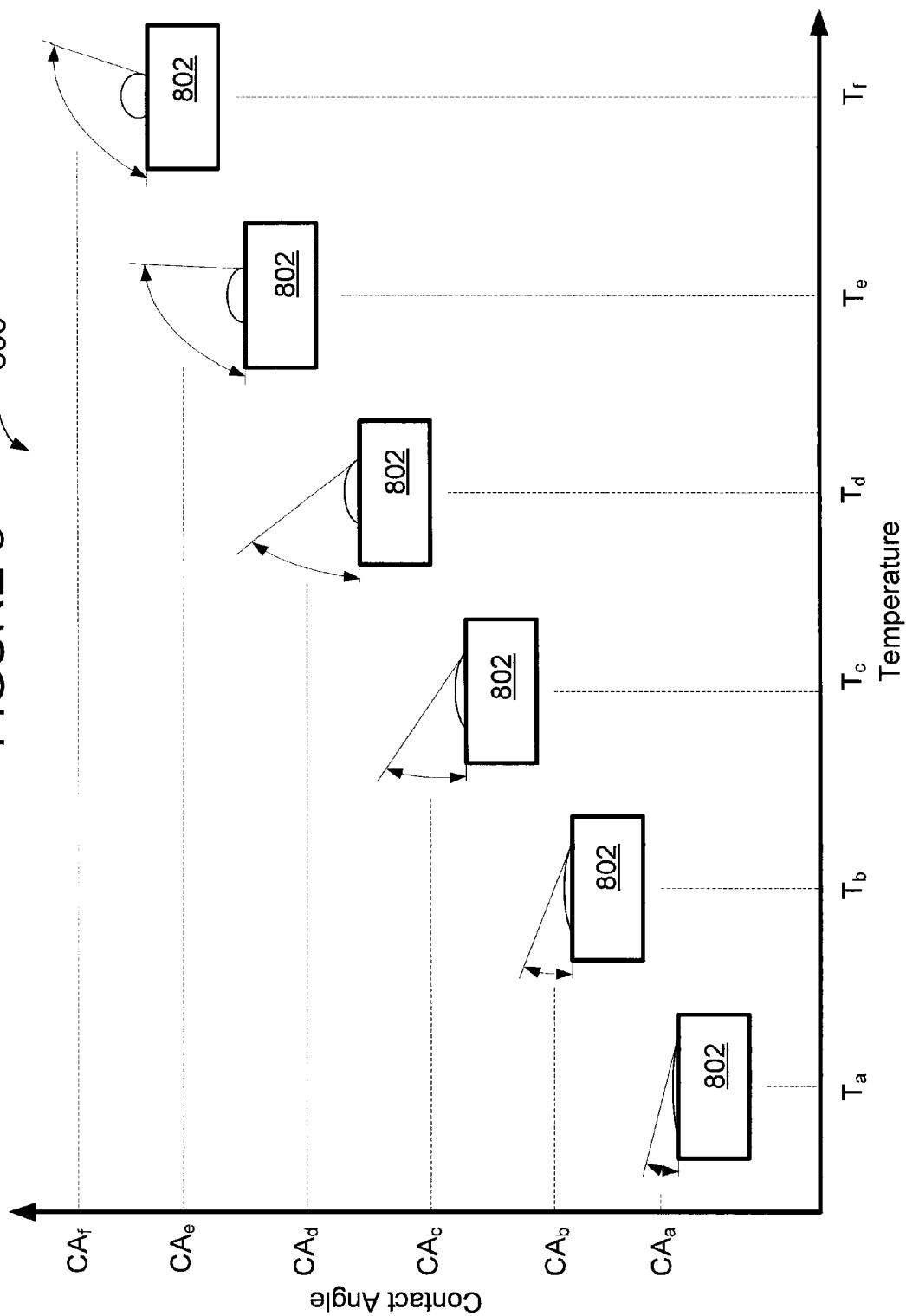
FIG. 8 shows a glass transition temperature test method with a single sample for use in the method of FIG. 1.

FIG. 8 shows a glass transition temperature test similar to the one of FIG. 5, but uses a single sample rather than a plurality of samples 800. The single sample 802 has, as described above, been treated with atmospheric plasma and wetted with a wetting material.

Data is gathered when the treated and wetted sample 802 is brought to a plurality of different temperatures $T_{a-f}$ and at each temperature the corresponding contact angle $CA_{a-f}$ is measured. In various embodiments, a dynamic system measures/scans temperature and contact angle in real time. And, in various embodiments, knowledge and/or estimates of the glass transition temperature of the polymer indicate an appropriate temperature range $T_{a-f}$.

The temperature versus contact angle data, obtained here from a single sample 802, is analyzed to identify the glass transition temperature of the polymer. As described in connection with FIG. 5, the onset of a sharply sloped central region of the temperature-contact angle curve indicates the glass transition temperature Tg has been reached.

Embodiments of the present invention can be used to determine Tg of various hydrophobic polymers. For example, embodiments of the present invention can be used in the quality control (QC) of thin films (ie. Paints, coatings, etc.), neat resins, and composite materials. The QC of composite surfaces as well as structural adhesives utilized for bonding is important in the fabrication of terrestrial and space hardware. In the past, a number of problems have occurred where large composite structures have become severely compromised during processing. The damaged zone was localized to the outer ply (25-100 μm) of a much thicker composite (12 mm). Even though state-of-the-art DMA instrumentation to measure Tg, these measurements failed to indicate problems because the bulk of the composite was not affected. Upon bonding this surface to other components, failure occurred substantially below expectations. In stark contrast to DMA, using the present invention to measure surface Tg would have revealed severe degradation of the composite structure.

While various embodiments of the present invention have been described above, it should be understood that they have been presented by way of example only, and not limitation. It will be apparent to those skilled in the art that various changes in the form and details can be made without departing from the spirit and scope of the invention. As such, the breadth and scope of the present invention should not be limited by the above-described exemplary embodiments, but should be defined only in accordance with the following claims and equivalents thereof.

What is claimed is:

1. A system for measuring glass transition temperature comprising:
    at least one sample containing hydrophobic polymeric material;
    a surface of the polymeric material treated with an atmospheric plasma;
    a wetting material on the treated surface;
    a contact angle defined by the wetting material and the treated surface;
    the contact angle changes in response to changes in polymeric material temperature; and,
    a device for determining a relationship between the changes in the contact angle corresponding to the changes in the polymeric material temperature, wherein said relationship is indicative of a glass transition temperature of the polymeric material;
wherein the system comprising a thermal device for changing the polymeric material temperature.

2. The system of claim 1 wherein the thermal device is a heater.

3. The system of claim 1 wherein the changes in polymeric material temperature are polymeric material temperature increases.

4. The system of claim 1 wherein said device determines an inflection point in the relationship between contact angle and the polymeric material temperature, the inflection point indicates the glass transition temperature.

5. The system of claim 1 wherein the polymeric material is a film.

6. The system of claim 1 wherein the polymeric material is a composite material.

7. A system for measuring glass transition temperature comprising:
   a hydrophobic polymeric material;
   a surface of the polymeric material treated with an atmospheric plasma;
   a heater for heating the polymeric material;
   a wetting material on the treated surface;
   a contact angle measuring device for measuring a contact angle defined by the wetting material and the treated surface; and,
   wherein the temperature of the polymeric material increases when the heater is operated and there is a corresponding increase in the contact angle indicating a glass transition temperature of the polymeric material.

8. A system for measuring glass transition temperature comprising:
   a sample containing hydrophobic polymeric material;
   a surface of the polymeric material treated with an atmospheric plasma;
   a wetting material on the treated surface;
   a thermal device for changing the temperature of the polymeric material; and,
   the wetting material and the treated surface interact to form a contact angle;
   wherein a glass transition temperature of the polymeric material is characterized by a relationship between contact angle and polymeric material temperature.

9. The system of claim 1 wherein for the at least one sample a plurality of sample temperatures and corresponding contact angles
   are indicative of the glass transition temperature of the polymeric material.

10. The system of claim 9 wherein the contact angles are less than 150 degrees.

* * * * *